Feb. 19, 1974 D. F. DAYTON ET AL Plant Pat. 3,488
APPLE TREE
Filed Sept. 1, 1972
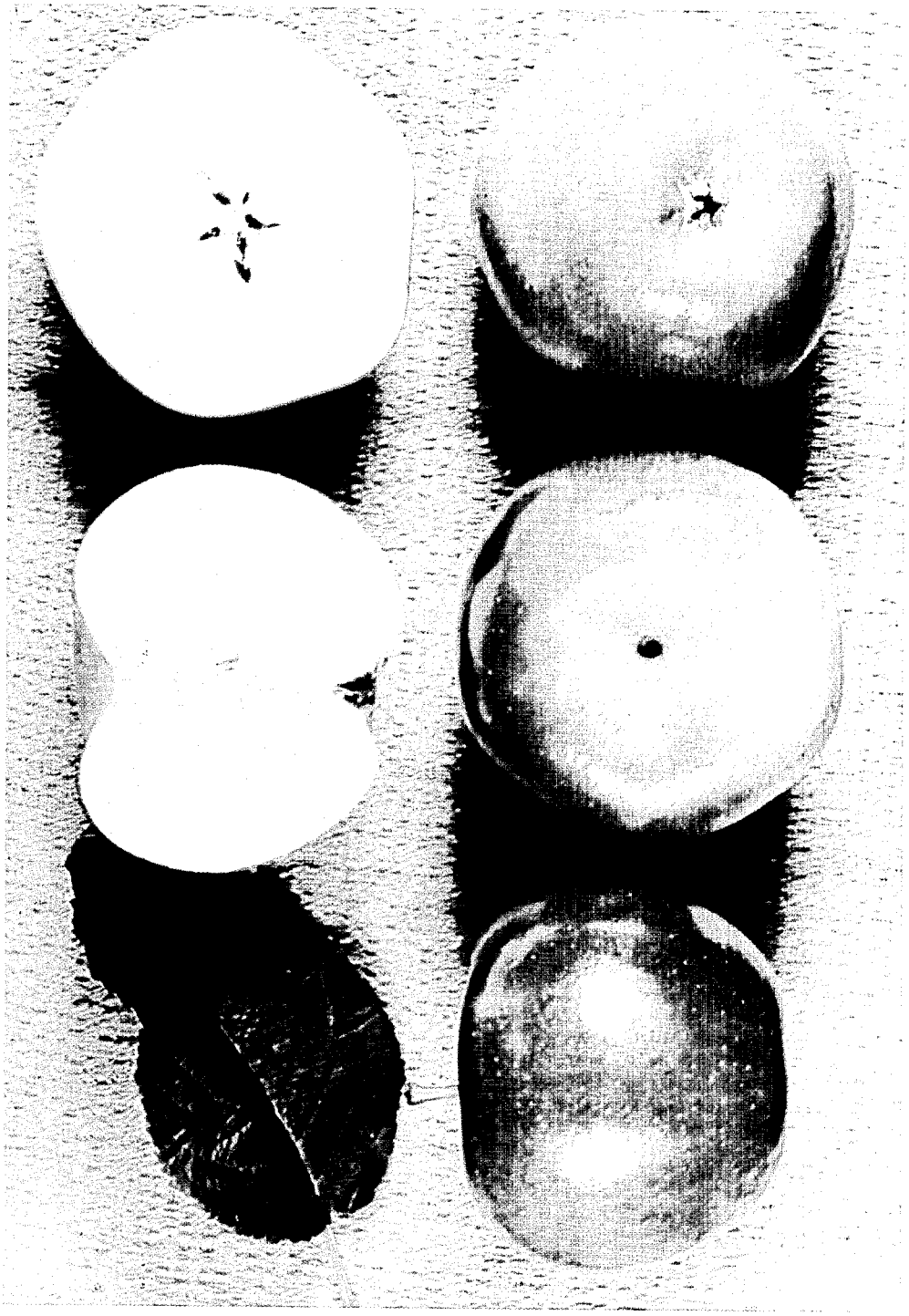

United States Patent Office

Plant Pat. 3,488
Patented Feb. 19, 1974

3,488
APPLE TREE

Daniel F. Dayton, Urbana, and James B. Mowry, Carbondale, Ill., L. Frederic Hough, Bloomsburg, and Catherine Bailey, Englishtown, N.J., Edwin B. Williams, Lafayette, and Jules Janick and Frank H. Emerson, West Lafayette, Ind., and J. Ralph Shay, Corvallis, Oreg., assignors to Purdue Research Foundation

Filed Sept. 1, 1972, Ser. No. 285,941
Int. Cl. A01h *5/03*
U.S. Cl. Plt.—34 1 Claim

This invention is a new and distinct cultivar of apple tree. It was discovered by applicants in September 1966 at Lafayette, Ind., in the course of an attempt to develop apple trees with high fruit quality and resistance to *Venturia inaequalis* (Cke,) Wint., the causal agent for the apple scab disease. The tree is a seedling of known parentage planted in 1962 in the Hinsley Breeding Orchard at the Horticulture Farm of the Department of Horticulture at the Purdue University Agricultural Experiment Station, Lafayette, Ind. In the above orchard, its position was Row 4, Tree 67, having the designation 1659–1 in the breeding records. This selection has also been known as Co-op 4.

The present new cultivar, which is named Priscilla, is a seedling produced from crossing "Starking Delicious" as the seed parent and the seedling 610–2 as the pollen parent in 1961 in Door County, Wis. This new cultivar carries a genetic factor, $V_f$, inherited from *Malus floribunda* 821 which causes it to be resistant to infection caused by *Venturia inaequalis*. The presence of this genetic factor has been repeatedly proven by controlled inoculation tests in the Purdue greenhouse of the seedling and of its offspring produced from controlled crosses. The complete pedigree is shown below:

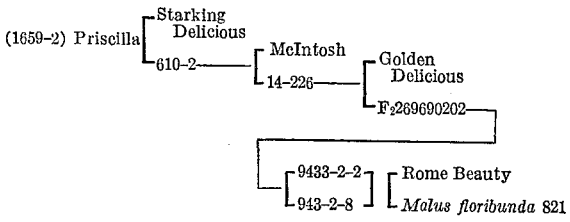

The new cultivar produces a moderately spreading and vigorous tree. The tree is productive and produces annually. It is resistant to scab and shows field resistance to fire blight and powdery mildew.

The tree flowers with or just after "McIntosh" and along with "Prima" which is described in U.S. Plant Pat. No. P.P. 3,134. The apple fruit has fine dessert quality, with crisp texture and pleasant flavor. The characteristic flavor is maintained 2–3 months or more at 34° F. There is little tendency of the fruit to drop before maturity.

After observation, the selection was asexually reproduced by grafting in seedling apple roots. The grafted material has maintained the described characteristic after propagation.

The accompanying drawing (color photograph) shows a typical example of fruit and foliage of Priscilla. The following is a detailed description of this new cultivar with the color designation according to the Horticultural Chart issued by the British Colour Council in collaboration with the Royal Horticultural Society:

*Flower*

Pedicel: 2.5 cm. (1 in.) in length.
Corolla: 4 cm. (1½ in.) diameter at anthesis.
Color: Solferino purple, ranging from plate 26 (tight bud) to 26/2 to paler in open flower. Outside of petal pigmented in patches at anthesis.

*Fruit*

Shape: Slightly oblate, regular.
Size: Axial diameter 5.8 to 6.0 cm. (2½ to 2¾ inches) transverse diameter 7 to 7.6 cm. (2¾ to 3 inches).
Color: Undercolor sap green (Plate 62/2–62/1) ripening to primrose yellow (Plate 602/1); overcolor 70 to 90% currant red blush (Plates 821 to 821/2).
Skin: Smooth, waxy with small white dots, medium thick but not tough; no russeting.
Stem: 3.2 cm. (1¼ in.), medium thickness.
Cavity: Acute, deep, medium width, smooth.
Basin: Shallow and narrow.
Calyx: Persistent, curved to upright, closed.
Calyx tube: Urn-shaped.
Stamens: Basal.
Core line: Meeting.
Core: Medium, closed, small.
Carpels: Elongated, mucronate, smooth.
Seed: Acute, not tufted.
Flesh:
*Texture.*—Medium grained, crisp, breaking.
*Quality.*—Very good, mild sub-acid, aromatic.
*Color.*—Primrose yellow (Plate 601–3).
Maturity season: Two weeks before "Delicious."
Keeping quality: Retains quality and texture 2–3 months or more at 34° F.
Use: Very good dessert apple.

*Tree*

Tree: Moderately spreading and vigorous. Frequently terminal growth is determinate ending in a flower bud, occasionally the following year's growth is bifurcated.
Leaves: Oval, crenate margin, apex acute, base slightly cordate; length to width ratio=1.5.

In particular our new cultivar apple is distinguished by its resistance to scab and its excellent dessert quality.

We claim:

1. A new and distinct apple tree substantially as shown and described particularly characterized by resistance to apple scab, excellent fresh fruit quality as regards flavor and crisp texture and maturing approximately two (2) weeks before "Delicious," one (1) week before "Jonathan," or one and one-half (1½) weeks after "Prima."

No references cited.

ROBERT E. BAGWILL, Primary Examiner